United States Patent [19]

Partika et al.

[11] Patent Number: 5,271,414
[45] Date of Patent: Dec. 21, 1993

[54] BIOPSY CANNULA HAVING NON-CYLINDRICAL INTERIOR

[75] Inventors: Lawrence Partika, Bridgewater; Richard S. Anderson, Wayne, both of N.J.

[73] Assignee: Becton, Dickinson and Company, Franklin Lakes, N.J.

[21] Appl. No.: 954,717

[22] Filed: Sep. 30, 1992

[51] Int. Cl.⁵ ............................................. A61B 10/00
[52] U.S. Cl. .................................................... 128/754
[58] Field of Search ..................... 128/751, 753, 754; 606/170; 604/264, 280, 282

[56] References Cited

U.S. PATENT DOCUMENTS

| | | | |
|---|---|---|---|
| 1,273,542 | 7/1918 | Schoder | 604/264 |
| 4,314,565 | 2/1982 | Lee | 128/754 |
| 4,600,014 | 7/1986 | Bercha | 128/754 |
| 4,753,640 | 6/1988 | Nichols et al. | 604/280 |
| 4,850,373 | 7/1989 | Zatloukal et al. | 128/754 |
| 5,005,585 | 4/1991 | Mazza | 128/754 |

*Primary Examiner*—Max Hindenberg
*Attorney, Agent, or Firm*—John L. Voellmicke

[57] ABSTRACT

A biopsy cannula and a method are provided for capturing and retrieving a specimen of soft tissue for subsequent diagnostic evaluation. The biopsy cannula defines a passageway of non-circular cross-section. The cannula is inserted into target tissue and rotated about the longitudinal axis of the cannula. The non-circular cross-sectional shape of the passageway in the cannula helps the cannula grippingly engage the tissue and cause the tissue to rotate with the cannula. Regions of the tissue adjacent the distal end of the cannula will be subjected to torque and will be severed from tissue outside the cannula. The cannula may then be withdrawn with the severed core of target tissue therein. The exterior of the cannula may be generally rounded or cylindrical in shape.

20 Claims, 4 Drawing Sheets

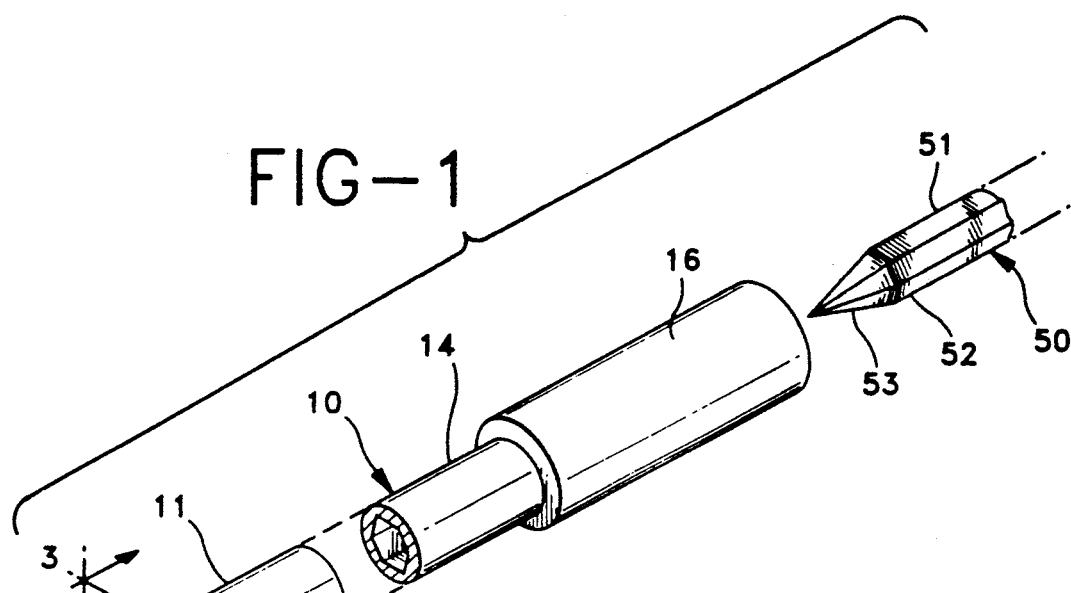
FIG-1
FIG-2
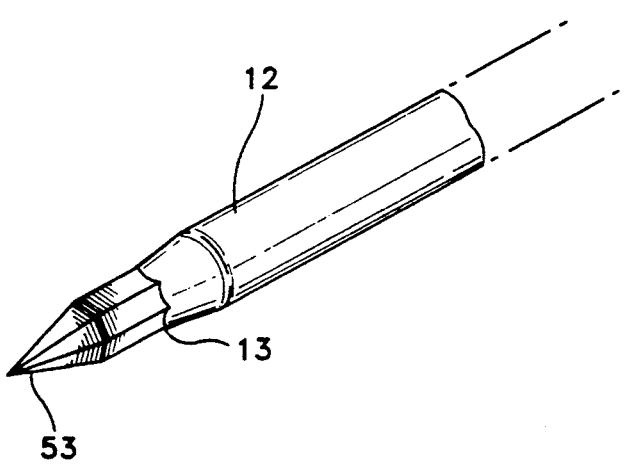
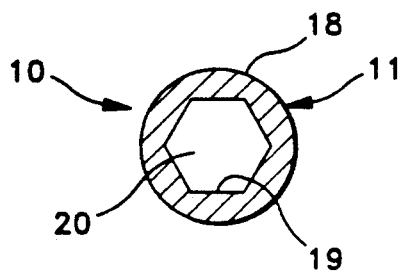
FIG-3
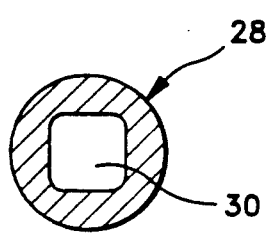
FIG-4
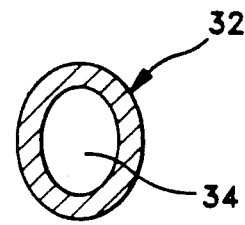
FIG-5

BIOPSY CANNULA HAVING NON-CYLINDRICAL INTERIOR

FIELD OF THE INVENTION

The present invention relates to a biopsy cannula which enables removal of a specimen or soft tissue from a patient for subsequent analysis.

DESCRIPTION OF THE PRIOR ART

Biopsies involve diagnostic evaluation of tissue removed from a patient. Some such evaluations require only a single cell or small groups of cells. Biopsies for these purposes utilize fine needle aspiration (FNA) techniques, where a vacuum applied to a small diameter cannula gathers a small number of cells. Other diagnostic evaluations, however, require larger tissue samples that must be removed from the patient. Physicians and laboratory technicians must balance the need for a relatively large tissue sample with the competing desire to minimize trauma for the patient.

Most cutting biopsies employ needle assemblies with several movable components to gather tissue and extract the gathered tissue from the patient. Some prior art cutting biopsy needles are manually operated, while others are at least semi-automatic. The functional cutting mechanisms of both manual and semi-automatic cutting biopsy needles typically are similar.

One prior art cutting biopsy needle includes a solid stylet of circular cross-section slidingly disposed within an outer cannula. The stylet is characterized by a sharpened point at its distal end and a transverse notch spaced proximally of the distal end. The stylet is inserted into the target tissue. When the stylet stops its forward motion, the tissue prolapses or fills the region defined by the notch. The outer cannula then is moved distally and severs the tissue that had prolapsed into the transverse notch of the stylet. The combined stylet and outer cannula then can be withdrawn from the patient, and the tissue trapped in the transverse notch of the stylet can be transported to a laboratory for appropriate diagnostic evaluation.

The above described prior art cutting biopsy needle with a notched stylet and an outer cannula will invariably obtain a sample. The volume of the tissue sample is defined by the depth of the notch, the length of the notch and the diameters of the stylet and outer cannula. Large tissue samples often are desired by the physician and laboratory technician. Larger samples can be obtained with the above described prior art cutting biopsy needle by increasing the depth of the notch, increasing the length of the notch and/or increasing the diameter of the stylet and cannula. However, larger diameter stylets and cannulas increase the trauma for the patient. Deeper or longer notches, on the other hand, can weaken the stylet enough to bend or break the stylet in the vicinity of the notch.

Another prior art cutting biopsy needle employs a sharpened cannula with a cylindrical passageway which slidingly receives a solid cylindrical pointed stylet therein. The stylet and cannula are assembled and advanced into the tissue as a unit. The pointed cannula is then advanced distally beyond the end of the stylet to cut and capture a cylindrical core of tissue in the portion of the passageway between the distal ends of the stylet and cannula. This cylindrical core of tissue will still be connected to other tissue at locations adjacent the distal end of the cannula. The prior art device then attempts to remove the captured core of tissue by applying a slight negative pressure at the proximal end of the cannula. The negative pressure is intended to hold the cylindrical core of tissue in the cannula and to sever the tissue adjacent the distal end of the cannula when the assembled cannula and stylet are withdrawn.

This prior art approach has the potential advantage of obtaining a fairly large tissue sample. However, several impracticalities and uncertainties exist. For example, the means for applying the proper amount of negative pressure can be cumbersome and costly. Second, the cylindrical core of tissue in the cannula is most likely to break at its weakest point, which often will not be at the distal end of the cannula. Thus, a fairly large tissue sample can be cut by this prior art apparatus, but only a small tissue samples may actually be withdrawn. Furthermore, the weak point at which the tissue sample breaks may well be at the necrotic center of the actual target lesion. Hence, a substantial portion of the actual target may be lost by the prior art cutting biopsy needle.

SUMMARY OF THE INVENTION

The subject invention is directed to a biopsy cannula for a cutting biopsy. The cannula has an elongate generally tubular wall with opposed proximal and distal ends. The tubular wall of the cannula is configured to define a passageway of non-circular cross-section for capturing a specimen of the target tissue. The particular cross-section for the passageway may be selected in accordance with dimensions of the cannula, characteristics of the material from which the cannula is made and characteristics of the target tissue. In preferred embodiments, the passageway is generally polygonal. However, the cannula also may be provided with a passageway of generally elliptical cross-section. The tubular wall of the subject biopsy cannula also defines an outer surface. As explained further herein, the outer surface of tubular wall of the cannula preferably is substantially cylindrical.

A biopsy cannula of the subject invention may be employed by inserting the cannula into the patient, such that a desired length of the target tissue is captured in the passageway. The cannula then can be rotated about its longitudinal axis. The non-circular cross-section of the passageway defined by the tubular wall of the cannula helps prevent the cannula from rotating independently of the core of tissue captured therein. Rather, the non-circular cross-sectional configuration of the passageway causes the captured core of tissue to be held by and rotate with the cannula. However, tissue outside of the passageway of the cannula will not be subject to the torque generated by rotation of the cannula. As a result the rotating core of the target tissue within the passageway of the cannula will be severed from the non-rotating tissue at a location adjacent the distal end of the cannula thereby maximizing the volume of the tissue sample. In the method of the present invention the outer surface of the tubular wall may also be non-circular.

The severed core of tissue captured within the cannula can be removed from the patient for subsequent diagnostic evaluation. In most instances frictional force between the tubular wall of the cannula and the tissue therein will be sufficient to retain the tissue in the cannula while the cannula is withdrawn from the patient. In some embodiments, however, means for providing a slight aspiration may be provided.

The tissue sample can be expelled onto a slide or into a container after the cannula has been withdrawn from the patient. This expulsion of the tissue sample can be effected either by a stylet in the cannula or by pressure from a syringe.

As noted above, it is desirable to minimize trauma to the patient. Trauma is reduced by providing a skin puncturing point on the distal end of the cannula. In embodiments wherein the exterior surface of the tubular wall is cylindrical the rotation of the cannula about its longitudinal axis will have minimal impact on tissue adjacent the exterior surface of the cannula.

The biopsy cannula is preferably formed from stainless steel or other metallic material. However, the cannula can be formed from a thermoplastic material such as by extrusion. The thermoplastic may be substantially transparent to enable a preliminary visual inspection and evaluation of the tissue sample immediately upon withdrawal from the patient. Such preliminary inspection typically would not replace a thorough diagnostic evaluation of the sample. However, the physician or technician obtaining the tissue sample may be able to visually determine whether the sample is adequate for diagnostic evaluation, and hence could make an instantaneous determination as to whether it is appropriate to take a second biopsy sample.

The cannula with the interior having a non-circular cross-section may be used with an introducer cannula dimensioned to telescopingly receive the biopsy cannula therein. The introducer cannula may be advanced into the tissue of the patient, and the biopsy cannula then can be advanced into the introducer cannula. This option enables plural biopsy cannula to be used sequentially with a single introducer cannula to sequentially withdraw plural tissue samples. Tissue samples at different axial positions along the introducer cannula can be analyzed separately.

BRIEF DESCRIPTION OF THE DRAWINGS

FIG. 1 is a perspective view of a biopsy cannula in accordance with the subject invention and a stylet;

FIG. 2 is a perspective view of the distal end of the biopsy cannula of FIG. 1 shown with the stylet positioned therein;

FIG. 3 is a cross-sectional view taken along line 2—2 in FIG. 1;

FIG. 4 is a cross-sectional view similar to FIG. 2 but showing a second embodiment of the biopsy cannula;

FIG. 5 is a cross-sectional view similar to FIG. 2 but showing a third embodiment of the subject biopsy cannula;

DETAILED DESCRIPTION OF THE PREFERRED EMBODIMENT

Figure 6:
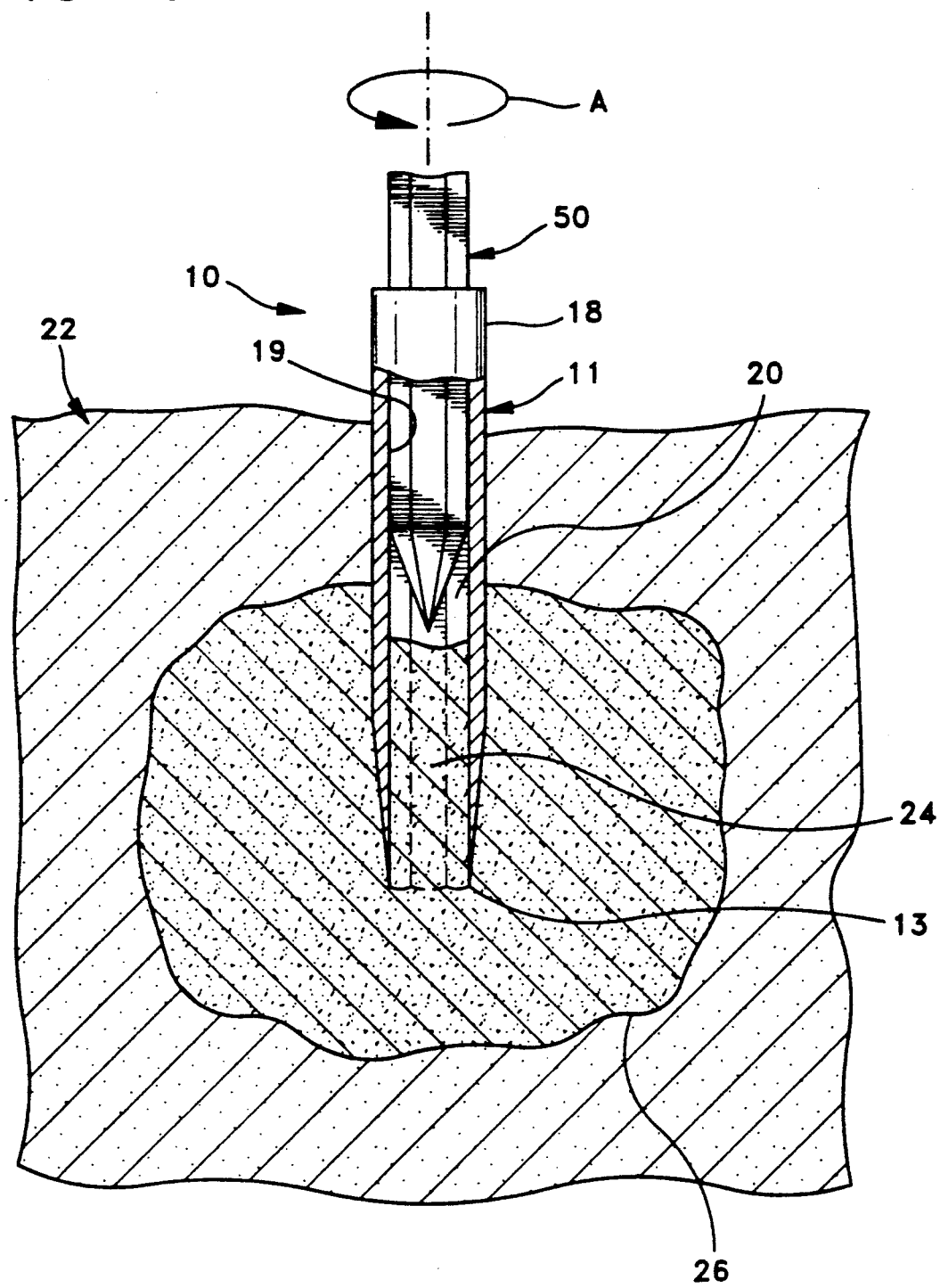
FIG. 6 is a partial cross-sectional view taken along the longitudinal axis of the cannula, and showing the cannula capturing a specimen of tissue.

A biopsy cannula in accordance with the subject invention is identified generally by the numeral 10 in FIG. 1. Cannula 10 includes an elongate tubular wall 11 having opposed distal and proximal ends 12 and 14 respectively. Distal end 12 is tapered at an angle to the longitudinal axis of tubular wall 11 to define a sharp edge 13. The edge is desirably substantially perpendicular to the longitudinal axes of said cannula. In this embodiment the edge is preferably scallop shaped. Proximal end 14 is mounted to a hub 16 which is configured to facilitate insertion and withdrawal of the cannula and rotation of the cannula about its longitudinal axis. Additionally, hub 16 is depicted for a biopsy cannula. Other hub configurations could be provided for manual biopsy procedures or for use with firing devices to provide automatic or semi-automatic specimen collection.

The tubular wall of biopsy cannula 10 preferably defines a smooth cylindrical outer surface 18 and an opposed inner surface 19 defining a passageway 20 of non-circular cross-section extending axially through the cannula. In a preferred embodiment, as shown most clearly in FIGS. 1-3, passageway 20 is of hexagonal cross-section. However, other generally polygonal or elliptical cross-sections may be provided for passageway 20, as explained herein.

A stylet 50, having an elongate body portion 51 which is sized and shaped to substantially occlude passageway 20 of the biopsy cannula when the stylet is placed therein as illustrated in FIG. 2. The stylet includes distal end 52 having a sharpened point 53. At the time of use, sharpened point 53 should be positioned distally of edge 13 on the biopsy cannula to provide a tissue penetrating point. In use, the assembly of the stylet and the biopsy cannula, as illustrated in FIG. 2, is forced through the patient's flesh so that stylet point 53 is at or near the periphery of the target tissue 24. At this time, as best illustrated in FIG. 6, the biopsy cannula is advanced distally into the target tissue while the stylet remains in its original position. Sharp edge 13 on the distal end of the biopsy cannula will cut generally circumferentially into tissue 22, such that a core of target tissue 24 will be captured in passageway 20 of tubular wall 11. The core of target tissue will assume a substantially prismatic shape with a cross-section generally conforming to the hexagonal cross-sectional shape of passageway 20.

After insertion of cannula 10 to an appropriate depth for capturing the target tissue, biopsy cannula 10 is rotated about its longitudinal axis as indicated by arrow "A" in FIG. 6. Portions of the tubular wall of biopsy cannula 10 defining hexagonal passageway 20 will grippingly engage the generally prismatic core of target tissue 24 in a manner similar to a hexagonal socket wrench gripping a hexagonal nut. More particularly, torque on biopsy cannula 10 will exert rotational forces on the core of target tissue 24 disposed within the hexagonal passageway 20. Consequently, the core of target tissue will tend to rotate with biopsy cannula 10. Torque will not be transmitted to tissue 22 external of biopsy cannula 10. As a result, the tissue will tend to twist and subsequently sever at region 26 adjacent distal end 12 of the biopsy cannula.

As noted above, it is desirable to minimize trauma imposed on a patient during a biopsy. Trauma is minimized by providing a generally rounded configuration for the exterior surface 18 of the biopsy cannula. More particularly, cylindrical exterior surface 18 will not grippingly engage tissue 22 adjacent thereto during the rotation of biopsy cannula 10 about its longitudinal axis.

The severed core of target tissue may be removed from the patient by merely withdrawing the biopsy cannula. Frictional forces between the core of target tissue and interior surface 19 of the tubular wall 11 generally will be sufficient to cause the captured core of target tissue to withdraw with the biopsy cannula. However, aspiration means such as a syringe may be provided in communication with proximal end 12 of tubular wall 11 to retain the core of tissue in passageway 20 during withdrawal of the cannula by providing a subatmospheric pressure in the passageway of the cannula.

The passageway of the biopsy cannula may have other non-cylindrical cross-sectional configurations in accordance with the subject invention. For example, other polygonal cross-sectional configurations may be provided, such as rectangular or octagonal. Additionally, as depicted in FIG. 4, a biopsy cannula 28 may be provided with a generally polygonal passageway 30 having rounded corners. The non-cylindrical cross-sectional shape of passageway 30 on biopsy cannula 28 will transmit rotational forces from cannula 28 to a core of tissue in substantially the same manner as the hexagonal passageway of biopsy cannula 10 depicted in FIGS. 1-3. As still another alternative, FIG. 5 depicts a biopsy cannula 32 having a passageway 34 of generally elliptical cross-sectional configuration. The ellipse defined by passageway 34 also will be effective in transmitting torque from cannula 32 to a core of target tissue captured therein. Biopsy cannula 32 also has an elliptically shaped outside surface.

Figure 7:
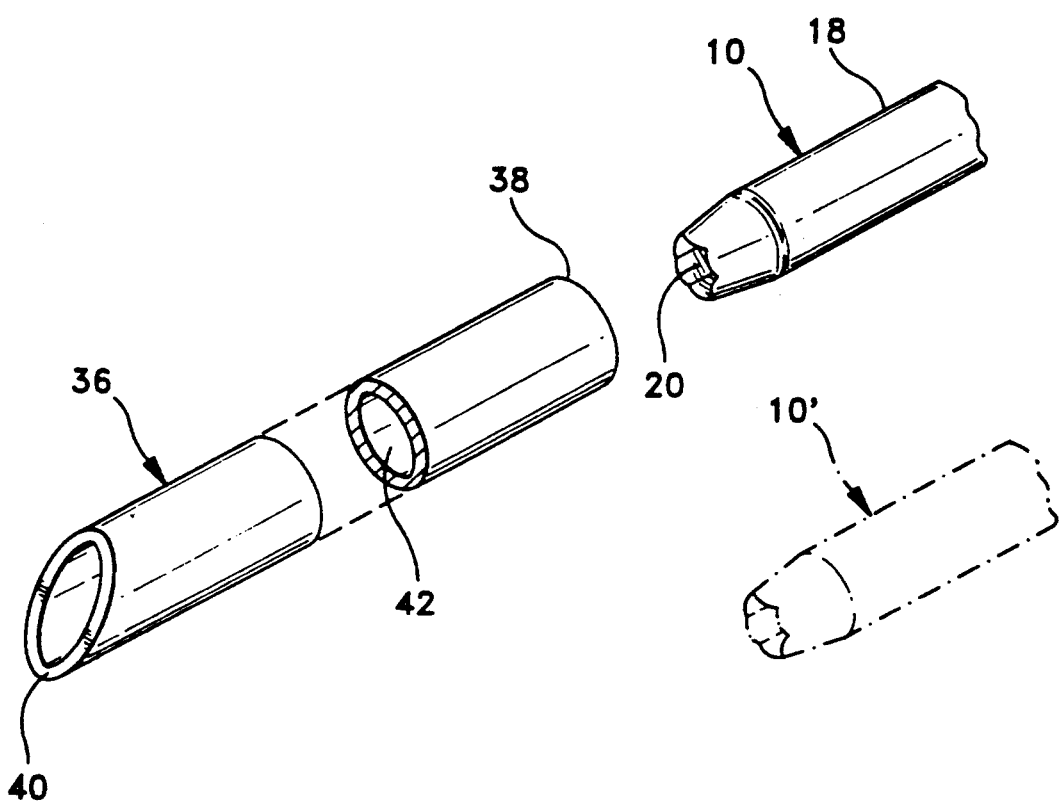
FIG. 7 is a perspective view showing a biopsy cannula and introducer cannula in accordance with the subject invention.
Figure 8:
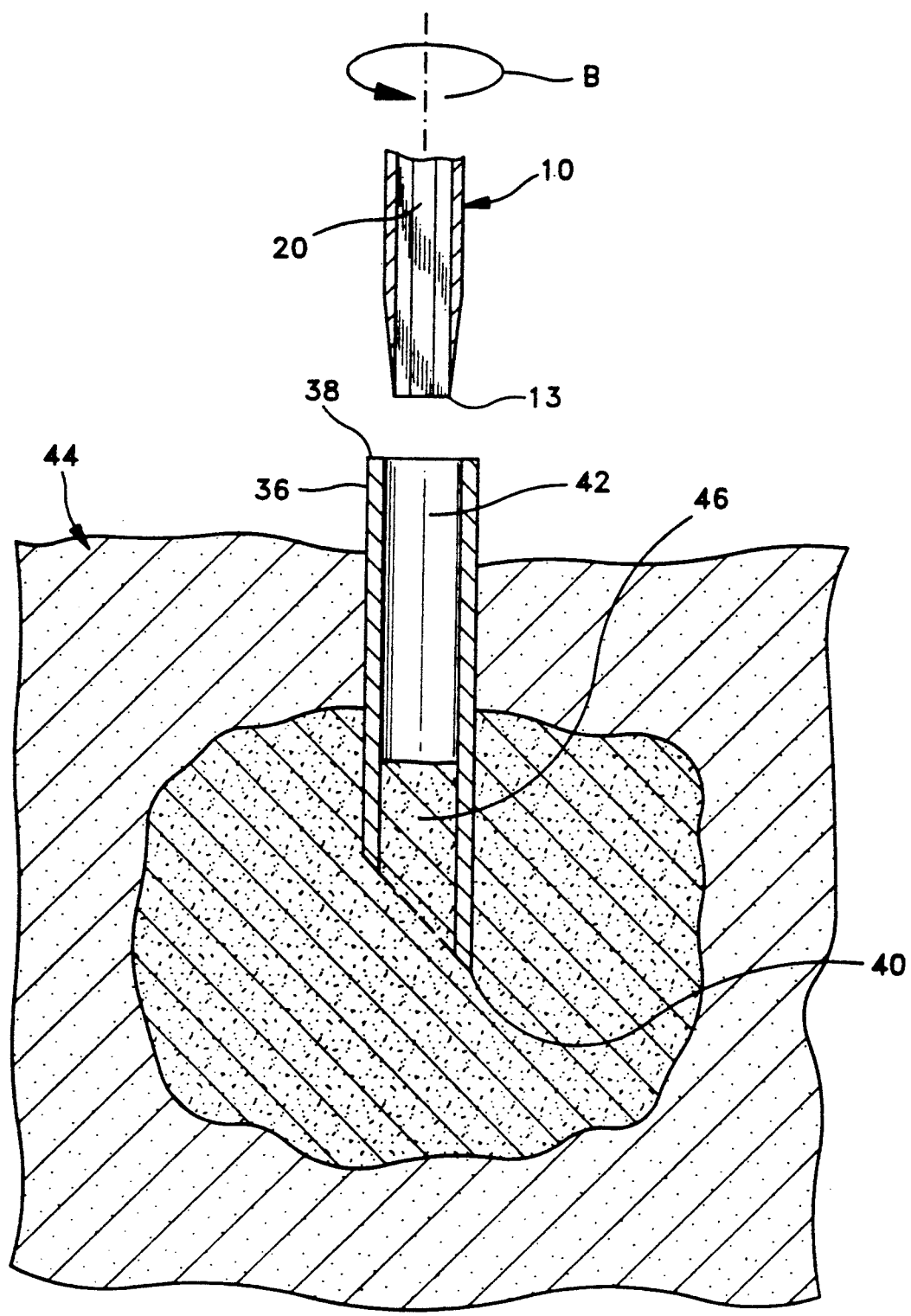
FIG. 8 is a cross-sectional view taken along the longitudinal axes of the biopsy cannula and the inserted cannula, and showing their use in a tissue.

The biopsy cannula of the subject invention may be used independently to obtain a tissue sample or in combination with an inserter cannula to enable extraction of one or more tissue samples for appropriate diagnostic evaluation. More particularly, as shown in FIG. 7, biopsy cannula 10 is employed with inserter cannula 36. The inserter cannula has opposed proximal and distal ends 38 and 40 and a passageway 42 extending therebetween. Passageway 42 is of generally cylindrical cross-sectional shape and defines a diameter approximately equal to or slightly larger than the external diameter defined by outer surface 18 of biopsy cannula 10. The inserter cannula may be employed with a plurality of biopsy cannula indicated as 10 and 10'. More particularly, the inserter cannula may be pierced through a region of target tissue 44 as shown in FIG. 8. The cylindrical passageway of inserter cannula 36 will capture a cylindrical core 46 of target tissue 44. A first of the biopsy cannulas may then be telescopingly slid into inserter cannula 36 to capture a tissue specimen therein. Biopsy cannula 10 may then be rotated about its longitudinal axis as indicated by arrow "B" in FIG. 7, such that the torque generated by the rotation severs a portion of core of the target tissue at a location approximately aligned with end 12 of biopsy cannula 10. As noted above, the torque generated in the core of tissue is attributable to the non-cylindrical cross-sectional shape of the interior of biopsy cannula 10.

Biopsy cannula 10 may then be withdrawn from inserter cannula 36 for subsequent diagnostic evaluation. A second biopsy cannula 10' may then be telescoped into inserter cannula 36 to a depth greater than the depth of the first target specimen. The second biopsy cannula may be used in exactly the manner described above to extract a second tissue specimen from a different axial position along inserter cannula 36. This may be repeated to extract several tissue specimens from different axial positions along the inserter cannula. The tissue specimens may be subjected to the same diagnostic evaluation for comparison to one another, or may be subjected to different diagnostic evaluations in view of their different positions in the body of the patient.

The stylet of the subject invention may be used to expel a tissue specimen from the biopsy cannula. More particularly, stylet 50 is dimensioned and configured to be slid into passage way 20 of cannula 10 as shown in FIG. 2. The stylet could be maintained separate from cannula 10 or in a retracted position during the capturing of the tissue, and could be slid in a distal direction after withdrawal of the cannula to expel the tissue for diagnostic evaluation.

What is claimed is:

1. A biopsy cannula comprising a tubular wall having opposed proximal and distal ends, and a passageway extending therethrough from said proximal end to said distal end, said tubular wall being configured such that at least the portion of said tubular wall adjacent said distal end includes said passageway having a non-circular cross-section and a substantially circular exterior surface.

2. The biopsy cannula as in claim 1, wherein said cross-section of said passageway through said cannula is of polygonal cross-sectional shape.

3. The biopsy cannula of claim 1, wherein said cross-section of said passageway through said cannula is of elliptical cross-sectional shape.

4. The biopsy cannula of claim 1, wherein said wall defines a substantially cylindrical exterior surface extending between said proximal and distal ends.

5. The biopsy cannula of claim 1, wherein said distal end is chamfered to define a sharp edge for cutting tissue.

6. The biopsy cannula of claim 1, wherein said non-circular cross-sectional shape of said passageway extends from said distal end to said proximal end of said tubular wall.

7. The biopsy cannula of claim 1 further comprising means for rotating said cannula engaged with said proximal end of said cannula.

8. The biopsy cannula of claim 7 wherein said means for rotating said cannula includes a rigid hub fixedly attached to said proximal end of said wall, said hub having a conduit therethrough in fluid communication with said passageway.

9. The biopsy cannula of claim 1 further comprising a stylet slidably insertable in the passageway for expelling a tissue specimen capture therein.

10. The biopsy cannula of claim 9 wherein said stylet includes a distal end having a sharp point.

11. The biopsy cannula of claim 1 formed from stainless steel.

12. The biopsy cannula of claim 1 formed from a thermoplastic material.

13. A biopsy cannula assembly for obtaining at least one biopsy specimen, said assembly comprising an inserter cannula having opposed proximal and distal ends and defining a cylindrical insert passageway extending therethrough from said proximal end to distal end; and at least one biopsy cannula having opposed proximal and distal ends and defining biopsy passageway extending between said proximal and distal ends, said biopsy cannula having a cylindrical exterior surface dimensioned for telescoping insertion of said biopsy cannula into the insert passageway of said inserter cannula, the biopsy passageway defined by said biopsy cannula being of non-circular cross-section at least in proximity to said distal end of said biopsy cannula.

14. A biopsy cannula assembly as in claim 13 comprising a plurality of said biopsy cannula alternately and sequentially insertable into said inserter cannula.

15. The biopsy cannula assembly of claim 13, wherein said cross-section of said passageway in said biopsy cannula is polygonal.

16. A biopsy method for capturing and withdrawing a specimen of tissue, said method comprising the steps of:

providing a biopsy cannula with opposed proximal and distal ends and having a passageway extending therebetween defining a longitudinal axis, at least the portion of said passageway adjacent said distal end of said passageway having a non-circular cross-section;

inserting said distal end of said cannula into a region of target tissue such that a portion of said target tissue is captured within said cannula;

rotating said cannula and said target tissue captured in said passageway about said longitudinal axis of said cannula sufficiently to separate portions of said target tissue in said passageway from portions of said target tissue external of said cannula; and withdrawing said cannula and said captured tissue for subsequent diagnostic evaluation.

17. The method of claim 16 wherein said distal end of said cannula includes a substantially non-circular exterior surface at its distal end.

18. The method of claim 16 further comprising the step of expelling the captured specimen from the cannula for said evaluation.

19. The method of claim 18, wherein the step of expelling the specimen from the cannula by sliding a stylet axially through the cannula.

20. The method as in claim 16 wherein said biopsy cannula includes a substantially cylindrical outside surface.

* * * * *